(12) United States Patent
Li et al.

(10) Patent No.: US 11,078,457 B2
(45) Date of Patent: Aug. 3, 2021

(54) *LYSINIBACILLUS FUSIFORMIS* WITH METHYLAMINE DEGRADABILITY AND APPLICATION THEREOF

(71) Applicant: Guangdong University of Technology, Guangzhou (CN)

(72) Inventors: Guiying Li, Guangzhou (CN); Shiai Li, Guangzhou (CN); Taicheng An, Guangzhou (CN); Yuetan Su, Guangzhou (CN); Xun'an Ning, Guangzhou (CN)

(73) Assignee: GUANGDONG UNIVERSITY OF TECHNOLOGY, Guangdong (CN)

( * ) Notice: Subject to any disclaimer, the term of this patent is extended or adjusted under 35 U.S.C. 154(b) by 122 days.

(21) Appl. No.: 16/491,919

(22) PCT Filed: Mar. 20, 2018

(86) PCT No.: PCT/CN2018/079519
§ 371 (c)(1),
(2) Date: Sep. 6, 2019

(87) PCT Pub. No.: WO2019/085370
PCT Pub. Date: May 9, 2019

(65) Prior Publication Data
US 2020/0377847 A1     Dec. 3, 2020

(30) Foreign Application Priority Data

Nov. 1, 2017   (CN) .......................... 201711058639.5

(51) Int. Cl.
*B09C 1/10*     (2006.01)
*C02F 3/34*     (2006.01)
(Continued)

(52) U.S. Cl.
CPC .............. *C12N 1/20* (2013.01); *B01D 53/84* (2013.01); *B09C 1/10* (2013.01); *C02F 3/32* (2013.01);
(Continued)

(58) Field of Classification Search
CPC ..................................... B09C 1/10; C02F 3/34
See application file for complete search history.

(56) References Cited

FOREIGN PATENT DOCUMENTS

| CN | 1145408 A | 3/1997 |
|---|---|---|
| CN | 104371954 A | 2/2015 |
| WO | 2011/104087 A1 | 9/2011 |

OTHER PUBLICATIONS

English-language machine translation of Chang et al., CN 107384834 A, 2017.*

(Continued)

*Primary Examiner* — Rosanne Kosson
(74) *Attorney, Agent, or Firm* — The Dobrusin Law Firm, P.C.

(57) ABSTRACT

The present invention discloses a strain of *Lysinibacillus fusiformis* with methylamine degradability and the application thereof. This strain, named *Lysinibacillus fusiformis* GDUTAN2, was deposited on May 24, 2017 in the China Center for Type Culture Collection in Wuhan University, Wuhan City, Hubei Province with a deposit number of CCTCC NO. M 2017284. This *Lysinibacillus fusiformis* GDUTAN2 was Grain-positive and rod-shaped, and the colony appeared to be round, white and transparent, having a diameter of 1-2 mm. The *Lysinibacillus fusiformis* GDUTAN2 of the present invention can be applied to environmental restoration, degrading methylamine in the environment at a high degradation efficiency. When it (Continued)

degraded methylamine for 96 h at a substrate concentration of 130 mg/L, the degradation efficiency could reach 32.8%.

4 Claims, 1 Drawing Sheet

Specification includes a Sequence Listing.

(51) Int. Cl.
    *C12N 1/20*     (2006.01)
    *B01D 53/84*     (2006.01)
    *C02F 3/32*     (2006.01)
    *C12R 1/01*     (2006.01)

(52) U.S. Cl.
    CPC .......... *B01D 2257/70* (2013.01); *C12N 1/205* (2021.05); *C12R 2001/01* (2021.05)

(56) References Cited

OTHER PUBLICATIONS

NCBI, Blastn, Blast2 sequence comparison of SEQ ID No. 1 and prior art seq., https://blast.ncbi.nlm.nih.gov/Blast.cgi, Feb. 24, 2021.*
Genbank Accession No. KY355612.1, Genbank, Feb. 20, 2017.

* cited by examiner

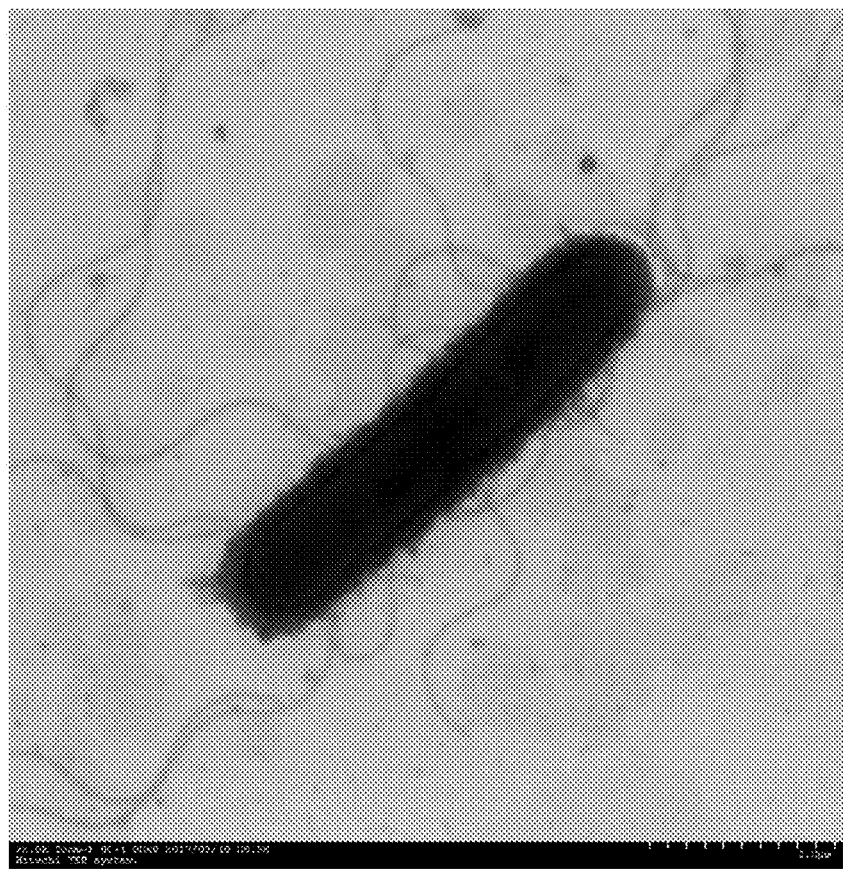

LYSINIBACILLUS FUSIFORMIS WITH METHYLAMINE DEGRADABILITY AND APPLICATION THEREOF

This application claims the priority of Chinese Patent Application No. 201711058639.5 that is entitled "*Lysinibacillus fusiformis* with Methylamine Degradability and Application Thereof" and was submitted to the China Patent Office on Nov. 1, 2017. The entire contents thereof are incorporated herein by reference.

FIELD OF THE INVENTION

The present invention belongs to the field of microbial technology, and more particularly relates to a strain of *Lysinibacillus fusiformis* with methylamine degradability and the application thereof.

BACKGROUND OF THE INVENTION

Odor pollution is a major problem in today's air pollution. Organic malodorous gases are mainly classified into sulfur-containing organic malodorous gases and nitrogen-containing organic malodorous gases, of which methylamine (MA) is a typical nitrogen-containing organic malodorous compound. Methylamine has an olfactory threshold as low as 0.021 ppm and is more difficult to biodegrade. It produces a strong irritating fish odor at low concentrations and is easily adsorbed by skin, clothing and the like. Methylamine can be absorbed through the respiratory tract, gastrointestinal tract and skin, and converted to dimethylamine or oxidized to form formic acid in the body. It has a strong stimulating and corrosive effect on the eyes, skin and respiratory mucosa, as well as a sympathomimetic effect on the whole body. It is often used in the production of drugs, organic nitrogen pesticides, dyes, explosives, surfactants, and so on. In the air of workplaces in China, methylamine has a short-term exposure allowable concentration of 0.01 ppm and a time-weighted average allowable concentration of 0.005 ppm.

At present, the treatment methods of methylamine at home and abroad mainly include physical methods and chemical methods. In contrast, the biodegradation of malodorous gases has the advantages of thorough degradation, low cost, and no secondary pollution, having attracted the attention of researchers at home and abroad. According to reports, due to the limited ability of single strains to degrade methylamine, some researchers have studied the degradation of methylamine by inoculating mixed strains. However, studies on the degradation of methylamine using new single strains have rarely been reported in the literature. Therefore, screening for high-efficiency, low-cost methylamine-degrading bacteria is of great significance for the purification of malodorous organic nitrogen-containing exhaust gas.

CONTENTS OF THE INVENTION

An object of the present invention is to provide a strain of *Lysinibacillus fusiformis* with methylamine degradability to overcome the deficiencies of the prior art. *Lysinibacillus fusiformis* GDUTAN2, belonging to a new variant of the *Bacillus* genus, has excellent methylamine degradability, and can degrade methylamine in the environment at a high degradation efficiency.

Another object of the present invention is to provide an application of the above-described *Lysinibacillus fusiformis* with methylamine degradability in environmental restoration.

The objects of the present invention are achieved by the following technical solution:

The present invention, in a first aspect, provides a strain of *Achromobacter xylosoxidans* with methylamine degradability named *Lysinibacillus fusiformis* GDUTAN2, which was deposited on May 24, 2017 in the China Center for Type Culture Collection in Wuhan University (No. 299 Bayi Road, Wuchang District, Wuhan City, Hubei Province) with a deposit number of CCTCC NO. M 2017284.

The morphological characteristics of the *Lysinibacillus fusiformis* with methylamine degradability of the present invention are as follows:

(a) By using the conventional physiological and biochemical identification methods of bacteria and electron microscopy, it was revealed that the *Lysinibacillus fusiformis* screened out was Grain-positive and rod-shaped with cell staining.

(b) Morphological characteristics of the colonies: After 24 h of culture in an LB solid medium, the colony appeared to be round, white and transparent, having a diameter of 1-2 mm The main physiological and biochemical characteristics of the *Lysinibacillus fusiformis* with methylamine degradability of the present invention are shown in Table 1 below:

TABLE 1

| Main physiological and biochemical characteristics of *Lysinibacillus fusiformis* | |
|---|---|
| Items | Test results |
| Arabinose | − |
| Xylose | − |
| Glucose | − |
| Mannitol | − |
| Citrate utilization | + |
| DNA hydrolysis | − |
| V-P test | − |
| Nitrate (reduction) | − |
| Starch hydrolysis | − |
| Gelatin liquefaction | − |
| Anaerobic growth | + |
| 2% NaCl growth | + |
| 5% NaCl growth | + |
| pH = 5.5 growth | + |
| pH = 9.0 growth | + |
| Gram staining | + |
| 50° C. growth | − |
| 15° C. growth | + |

The 16S rDNA sequence of the *Lysinibacillus fusiformis* with methylamine degradability of the present invention is set forth in SEQ ID NO: 1.

By alignment analysis of the 16S rDNA sequence, it was found that the homology between the strain of the present invention and *Lysinibacillus fusiformis* KNUC423 was as high as 100%. By combining the morphological characteristics, growth conditions, and physiological and biochemical identification results of the bacteria, it was determined that *Lysinibacillus fusiformis* GDUTAN2 belonged to a new variant of the *Bacillus* genus and was so named.

The present invention, in a second aspect, provides an application of the *Lysinibacillus fusiformis* with methylamine degradability in environmental restoration.

The *Lysinibacillus fusiformis* with methylamine degradability of the present invention is capable of degrading methylamine in the environment when used in environmental restoration.

Further, the environment includes atmosphere, water or soil.

Compared with the prior art, the present invention has the following beneficial effects:

1. The strain of *Lysinibacillus fusiformis* GDUTAN2 of the present invention was screened for the first time out of the landfill leachate of a landfill in Guangzhou City, Guangdong Province, having methylamine degradability.

2. The *Lysinibacillus fusiformis* GDUTAN2 of the present invention has the ability to efficiently degrade methylamine; when it degraded methylamine for 96 h at a substrate concentration of 5 mg/L, the degradation efficiency could reach 96.3%.

BRIEF DESCRIPTION OF THE DRAWINGS

FIG. 1 shows the morphology of *Lysinibacillus fusiformis* GDUTAN2 of the present invention under an electron microscope.

DETAILED DESCRIPTION OF THE EMBODIMENTS

The present invention will be further described with reference to the following specific examples, but these examples should not be construed as limiting the present invention. Unless otherwise specified, the technical means used in the examples are conventional means well known to those skilled in the art. Unless otherwise indicated, the reagents, methods, and devices employed in the present invention are routine in the art.

EXAMPLE 1

A strain of *Lysinibacillus fusiformis* with methylamine degradability, named *Lysinibacillus fusiformis* GDUTAN2, was deposited on May 24, 2017 in the China Center for Type Culture Collection in Wuhan University (No. 299 Bayi Road, Wuchang District, Wuhan City, Hubei Province) with a deposit number of CCTCC NO. M 2017284.

The *Lysinibacillus fusiformis* GDUTAN2 of the present example was isolated and screened from leachate of a landfill in Guangzhou City, Guangdong Province. The isolation and purification methods were as follows: The acclimation medium used was an inorganic salt medium (each 1000 mL of the inorganic salt medium contained $K_2HPO_4 \cdot 3H_2O$ 1.2 g, $KH_2PO_4$ 1.2 g, $NH_4Cl$ 0.4 g, $MgSO_4 \cdot 7H_2O$ 0.2 g, $FeSO_4 \cdot 7H_2O$ 0.01 g, and 1 mL of a trace element solution, wherein the trace element solution contained $CaCl_2 \cdot 2H_2O$ 0.2 g, $MnSO_4 \cdot 4H_2O$ 0.2 g, $CuSO_4 \cdot 2H_2O$ 0.01 g, $ZnSO_4 \cdot 7H_2O$ 0.2 g, $CoCl_2 \cdot 6H_2O$ 0.09 g, $Na_2MoO_4 \cdot 2H_2O$ 0.12 g, and $H_3BO_3$ 0.006 g). First, 1 mL of the landfill leachate was taken and diluted 100 times, inoculated into a nutrient broth, and aerobically cultured at 37° C. for 1 day in a shaker at a rotational speed of 150 rpm. Then, 1 mL of the enriched bacterial solution was taken and inoculated in an inorganic salt nutrient solution containing methylamine, and aerobically cultured at 37° C. for 5 days in a shaker at a rotational speed of 150 rpm, and then moved to the next concentration in an inoculating amount of 10%, with the substrate acclimation gradients respectively at 10, 20, 50 and 100 mg/L. The final-concentration acclimation solution was diluted by $10^{-1}$ to $10^{-6}$, 200 µL of the dilutions diluted by $10^{-5}$ and $10^{-6}$ was respectively applied to a solid agar plate with methylamine as the sole carbon source (the solid medium containing methylamine was obtained by adding 18 g of agar and 4 mg of methylamine to per liter of the above inorganic salt medium), and the plate was placed into an incubator to culture at 35° C. for 3 days. A single colony of different morphology was selected for determination of the degradation efficiency of methylamine, and the strain with the highest degradation efficiency was selected for purification.

Determination of degradation efficiency: Sampling periodically during the biodegradation of methylamine, and determining the degradation efficiency spectrophotometrically. Degradation efficiency=(initial concentration−final concentration)/initial concentration.

Spectrophotometric determination of methylamine concentration: Taking a certain amount of methylamine degradation solution into a 10 mL colorimetric tube, diluting to 2.0 mL with an absorption solution (0.01 M HCl), and adding 4.0 mL of a buffer (obtained by dissolving 4.08 g of potassium dihydrogen phosphate and 1.6 g of borax in 80 mL of distilled water, adding 6.35 mL of 5.0 M NaOH solution, and diluting to 100 mL with water) and 0.4 mL of diazonium salt solution (obtained by adding 1.0 mL of sodium nitrite solution to 10 mL of p-nitrophenylamine hydrochloride solution and mixing), respectively, shaking well, letting stand for 40 min, adding 1.0 mL of 5 M NaOH solution, mixing, letting stand for 20 min, and performing colorimetric quantification at 510 nm.

The purified colonies were identified, with the results as follows:

(1) Morphological Characteristics of the Bacteria:

a. By using the conventional physiological and biochemical identification methods of bacteria and electron microscopy, it was revealed that the *Lysinibacillus fusiformis* screened out was Grain-positive with cell staining; under the electron microscope, the bacterium was rod-shaped with flagella around, and had a size of (1.1 to 1.4) µm×(2.3 to 6.0) µm, as shown in FIG. 1;

b. morphological characteristics of the colonies: after 24 h of culture in an LB solid medium, the colony appeared to be neatly edged, round, white and transparent, having a diameter of 1-2 mm; and c. the main physiological and biochemical characteristics of *Lysinibacillus fusiformis* are shown in Table 2.

TABLE 2

| Physiological and biochemical characteristics of *Lysinibacillus fusiformis* | |
|---|---|
| Items | Test results |
| Arabinose | − |
| Xylose | − |
| Glucose | + |
| Mannitol | − |
| Citrate utilization | + |
| DNA hydrolysis | − |
| V-P test | − |
| Nitrate (reduction) | − |
| Starch hydrolysis | − |
| Gelatin liquefaction | + |
| Anaerobic growth | + |
| 2% NaCl growth | + |
| 5% NaCl growth | + |
| pH = 5.5 growth | + |
| pH = 9.0 growth | + |
| Gram staining | + |
| 50° C. growth | − |
| 15° C. growth | + |

The above results indicate that the selected bacteria of the present invention had physiological and biochemical characteristics very similar to those of the *Lysinibacillus fusiform* is genus.

(2) Extracting Bacterial Genomic DNA and using Bacterial 16S rDNA Universal Primers:

```
Upstream primer: F27
(5'-AGTTTGATCMTGGCTCAG-3')

Downstream primer: R1492
(5'-GGTTACCTTGTTACGACTT-3')
```

The entire 16S rDNA gene was amplified, with the sequencing results as shown in SEQ ID NO: 1.

By aligning the 16S rRNA gene sequence of 1398 bp in length as shown in SEQ ID NO: 1 with the gene sequence registered in the Genbank, it was found that the homology between the strain and *Lysinibacillus fusiformis* KNUC423 was up to 100%.

Based on the above physiological and biochemical characteristics and 16S rRNA gene sequence results, the strain of the present invention obtained by screening should belong to a new variant of the *Bacillus* genus, and was named *Lysinibacillus fusiformis* GDUTAN2.

The *Lysinibacillus fusiformis* GDUTAN2 was deposited on May 24, 2017 in the China Center for Type Culture Collection (CCTCC) in Wuhan University (No. 299 Bayi Road, Wuchang District, Wuhan City, Hubei Province) with a deposit number of CCTCC NO. M 2017284.

EXAMPLE 2

In this example, *Lysinibacillus fusiformis* GDUTAN2 was applied to environmental restoration, and could degrade methylamine in the environment. The environment includes atmosphere, water or soil.

The methylamine degradability of the selected *Lysinibacillus fusiformis* GDUTAN2 of the present invention was tested as follows:

The inorganic salt medium was prepared according to the needs of the degradation experiment: Adding 100 mL of an inorganic salt solution to a 300 mL serum bottle (per 100 mL of the inorganic salt solution contained $K_2HPO_4 \cdot 3H_2O$ 0.12 g, $KH_2PO_4$ 0.12 g, $NH_4Cl$ 0.04 g, $MgSO_4 \cdot 7H_2O$ 0.02 g, $FeSO_4 \cdot 7H_2O$ 0.001 g, $CaCl_2 \cdot 2H_2O$ 0.02 g, $MnSO_4 \cdot 4H_2O$ 0.02 g, $CuSO_4 \cdot 2H_2O$ 0.001 g, $ZnSO_4 \cdot 7H_2O$ 0.02 g, $CoCl_2 \cdot 6H_2O$ 0.009 g, $Na_2MoO_4 \cdot 2H_2O$ 0.012 g, $H_3BO_3$ 0.0006 g, and double distilled water 100 mL), and autoclaving at 121° C. for 30 min. First, activating the selected *Lysinibacillus fusiformis* GDUTAN2 with methylamine degradability in a nutrient broth medium (beef cream 3.0 g/L, peptone 10.0 g/L, and NaCl 5.0 g/L) at 30° C. for 24 h in a shaker at 100 rpm; and then, centrifuging the bacterial solution, collecting the bacteria, washing three times with a phosphate buffer, resuspending in 10 mL of an inorganic salt solution, and inoculating 1.0 mL of the bacterial solution into 100 mL of the inorganic salt solution containing different concentrations of methylamine; wherein the concentration of methylamine was 5, 10, 40, 70, 100 and 130 mg/L, respectively, the pH of the inorganic salt was 7, the reaction was carried out at 30° C. for 96 h in the shaker at 100 rpm, and sampling was made periodically to determine the degradation efficiency spectrophotometrically. The degradation efficiency was measured in the same way as in Example 1, and the results are shown in Table 3.

TABLE 3

Degradation efficiencies of different initial concentrations of methylamine degraded by *Lysinibacillus fusiformis* GDUTAN2

| Methylamine concentration (mg/L) | Degradation rate |
| --- | --- |
| 5 | 96.3% |
| 10 | 88.1% |
| 40 | 70.6% |
| 70 | 52.2% |
| 100 | 37.3% |
| 130 | 32.8% |

As can be seen from Table 3, the *Lysinibacillus fusiformis* GDUTAN2 screened out by the present invention could degrade methylamine under this condition up to 96.3%.

The above examples are preferred embodiments of the present invention, but the embodiments of the present invention are not limited thereto, and any other alterations, modifications, substitutions, combinations, and simplifications made without departing from the spirit and principle of the present invention should all be equivalent replacements and included in the scope of protection of the present invention.

The invention claimed is:

1. A method for degrading methylamine, comprising:
a) applying an effective amount of composition comprising *Lysinibacillus fusiformis* GDUTAN2 to a substrate containing methylamine, wherein the *Lysinihaciiius fusiformis* GDUTAN2 was deposited on May 24, 2017 in the China Center for Type Culture Collection in Wuhan University Wuhan City, Hubei Province with a deposit number of CCTCC NO. M 2017284; and
b) contacting the substrate with the composition comprising *L. fusiformis* GDUTAN2 for a sufficient length of time to degrade the methylamine.

2. The method according to claim 1, wherein the 16S rDNA sequence of the *Lysinibacillus fusiformis* GDUTAN2 is set forth in SEQ ID NO:1.

3. The method according to claim 1, wherein the substrate includes atmosphere, water or soil.

4. The method according to claim 2, wherein the substrate includes atmosphere, water or soil.

* * * * *

SEQUENCE LISTING

```
<160> NUMBER OF SEQ ID NOS: 1

<210> SEQ ID NO 1
<211> LENGTH: 1398
<212> TYPE: DNA
<213> ORGANISM: Lysinibacillus fusiformis

<400> SEQUENCE: 1
cagtcgagcg aacagagaag gagcttgctc cttcgacgtt agcggcggac gggtgagtaa      60
cacgtgggca acctacctta tagtttggga taactccggg aaaccggggc taataccgaa     120
taatctgttt cacctcatgg tgaaacactg aaagacggtt tcggctgtcg ctataggatg     180
ggcccgcggc gcattagcta gttggtgagg taacggctca ccaaggcgac gatgcgtagc     240
cgacctgaga gggtgatcgg ccacactggg actgagacac ggcccagact cctacgggag     300
gcagcagtag ggaatcttcc acaatgggcg aaagcctgat ggagcaacgc cgcgtgagtg     360
aagaaggatt tcggttcgta aaactctgtt gtaagggaag aacaagtaca gtagtaactg     420
```

```
gctgtacctt gacggtacct tattagaaag ccacggctaa ctacgtgcca gcagccgcgg    480
taatacgtag gtggcaagcg ttgtccggaa ttattgggcg taaagcgcgc gcaggtggtt    540
tcttaagtct gatgtgaaag cccacggctc aaccgtggag ggtcattgga aactgggaga    600
cttgagtgca gaagaggata gtggaattcc aagtgtagcg gtgaaatgcg tagagatttg    660
gaggaacacc agtggcgaag gcgactatct ggtctgtaac tgacactgag gcgcgaaagc    720
gtggggagca aacaggatta gataccctgg tagtccacgc cgtaaacgat gagtgctaag    780
tgttaggggg tttccgcccc ttagtgctgc agctaacgca ttaagcactc cgcctgggga    840
gtacggtcgc aagactgaaa ctcaaaggaa ttgacggggg cccgcacaag cggtggagca    900
tgtggtttaa ttcgaagcaa cgcgaagaac cttaccaggt cttgacatcc cgttgaccac    960
tgtagagata tagtttcccc ttcgggggca acggtgacag gtggtgcatg gttgtcgtca   1020
gctcgtgtcg tgagatgttg ggttaagtcc cgcaacgagc gcaacccttg atcttagttg   1080
ccatcattta gttgggcact ctaaggtgac tgccggtgac aaaccggagg aaggtgggga   1140
tgacgtcaaa tcatcatgcc ccttatgacc tgggctacac acgtgctaca atggacgata   1200
caaacggttg ccaactcgcg agagggagct aatccgataa agtcgttctc agttcggatt   1260
gtaggctgca actcgcctac atgaagccgg aatcgctagt aatcgcggat cagcatgccg   1320
cggtgaatac gttcccgggc cttgtacaca ccgcccgtca caccacgaga gtttgtaaca   1380
cccgaagtcg gtgaggta                                                 1398
```